United States Patent
Kudo et al.

(10) Patent No.: US 6,972,132 B1
(45) Date of Patent: Dec. 6, 2005

(54) SYSTEM FOR RELEASE IN LOWER DIGESTIVE TRACT

(75) Inventors: Yumio Kudo, Tokyo (JP); Hiroki Ueshima, Tokyo (JP); Kazuya Sakai, Tokyo (JP)

(73) Assignee: Mochida Pharamceutical Co., Ltd., Tokyo (JP)

( * ) Notice: Subject to any disclaimer, the term of this patent is extended or adjusted under 35 U.S.C. 154(b) by 0 days.

(21) Appl. No.: 10/009,265

(22) PCT Filed: Jun. 9, 2000

(86) PCT No.: PCT/JP00/03770

§ 371 (c)(1),
(2), (4) Date: Dec. 10, 2001

(87) PCT Pub. No.: WO00/74720

PCT Pub. Date: Dec. 14, 2000

(30) Foreign Application Priority Data

Jun. 9, 1999 (JP) ................................. 11-199409

(51) Int. Cl.[7] .......................... A61K 9/36; A61K 9/62; A61K 9/16
(52) U.S. Cl. ...................... 424/461; 424/479; 424/488; 424/493; 424/499
(58) Field of Search .............................. 424/451, 452, 424/457, 458, 459, 460, 461, 462, 463, 464, 424/465, 468, 470, 474, 475, 479, 480, 481, 424/482, 484, 485, 486, 487, 488, 489, 490, 424/491, 493, 494, 495, 496, 497, 498

(56) References Cited

U.S. PATENT DOCUMENTS 4,522,625 A * 6/1985 Edgren ...................... 424/473

| | | | |
|---|---|---|---|
| 4,871,549 A | 10/1989 | Ueda et al. | |
| 5,057,317 A * | 10/1991 | Iida ............................. | 424/423 |
| 5,217,720 A | 6/1993 | Sekigawa et al. | |
| 5,283,064 A | 2/1994 | Suzuki et al. | |
| 5,342,624 A | 8/1994 | McNeill et al. | |
| 5,407,682 A | 4/1995 | Schacht et al. | |
| 5,516,530 A * | 5/1996 | Lo et al. ...................... | 424/473 |
| 5,840,332 A | 11/1998 | Lerner et al. | |
| 6,004,583 A * | 12/1999 | Platé et al. .................. | 424/486 |
| 6,214,378 B1 | 4/2001 | Tanida et al. | |

(Continued)

FOREIGN PATENT DOCUMENTS

EP 284039 A2 9/1988

(Continued)

OTHER PUBLICATIONS

Hawley's Condensed Chemical Dictionary, 1993; p 236.*

(Continued)

Primary Examiner—Gollamudi S. Kishore
(74) Attorney, Agent, or Firm—Birch, Stewart, Kolasch & Birch, LLP

(57) ABSTRACT

A system whereby a substance which is orally taken and to be delivered into the lower digestive tract is selectively delivered into the lower digestive tract. More particularly, a system which makes it possible to surely and quickly deliver the aimed substance to the lower digestive tract without being affected by pH change in the digestive tract due to change in bacterial flora. Compositions disintegrating in the lower digestive tract characterized by containing a compound <A>, which has a molecular weight of 1000 or less and has a disulfide bond, and a polymer <B>, which has a molecular weight exceeding 1000 and is digested by enteric bacteria and/or undergoes softening, swelling or dissolution due to a decrease in pH; molded products with the use of these compositions; and preparations with the use of these molded products.

8 Claims, 7 Drawing Sheets

U.S. PATENT DOCUMENTS

| | | |
|---|---|---|
| 6,248,362 B1 | 6/2001 | Tominaga et al. |
| 6,368,629 B1 | 4/2002 | Watanabe et al. |
| 6,413,494 B1 | 7/2002 | Lee et al. |

FOREIGN PATENT DOCUMENTS

| | | |
|---|---|---|
| JP | 4-41422 A | 2/1992 |
| JP | 4247026 | 9/1992 |
| JP | 5-508631 A | 12/1993 |
| JP | 10-324642 A | 12/1998 |
| WO | WO 91/11175 | 8/1991 |
| WO | WO 91/16881 | 11/1991 |
| WO | WO 95/28963 | 2/1995 |
| WO | 95/35100 A1 | 12/1995 |
| WO | 96/10994 A1 | 4/1996 |

OTHER PUBLICATIONS

Kopecek, J. et al, Pharmaceutical Research, vol. 9, No. 12, pp. 1540-1545; 1992.

Kimura, Y. et al., Polymer, vol. 33, No. 24, pp. 5294-5299; 1992.

W. G. Cook et al., Pharmaceutical Research, vol. 10, No. 10, S223; 1993.

\* cited by examiner

| | stomach | duodenum | jejunum | ileum | cecum | colon | excreta |
|---|---|---|---|---|---|---|---|
| 4h | 🥚🥚🥚 | | | | | | |
| 6h | 🥚🥚🥚 | | | | | | |
| 8h | 🥚 | 🥚 | oo o | | | | |
| 10h | | | | oo o | ⊛⊛ ⊛⊛⊛ | | |
| 12h | | | | | ●●⊛ ●●● ●●⊂ | | |
| 14h | | | | | ●●● ⊂⊂ | ⊂ o | |
| 24h | | | | | | | ⊂⊂⊂ ⊂⊂⊂ |

Enteric capsule not disintegrated o  Unchanged seamless soft capsule

⊛  Browned seamless soft capsule

●  Blackened seamless soft capsule (film strength decreased)

⊂  Burst seamless soft capsule (content liquid leaked)

SYSTEM FOR RELEASE IN LOWER DIGESTIVE TRACT

This application is the national phase under 35 U.S.C. § 371 of PCT International Application No. PCT/JP00/03770 which has an International filing date of Jun. 9, 2000, which designated the United States of America.

TECHNICAL FIELD

The present invention relates to a system that orally uptakes a material desired to be delivered to a lower part of the gastrointestinal tract and delivers it selectively to the lower part of gastrointestinal tract. More specifically, the present invention relates to a system that unfailingly and quickly delivers an objective material selectively to a lower part of gastrointestinal tract without being influenced by a change in pH in the gastrointestinal tract due to a variation in the bacterial flora. Also, the present invention relates to a composition that disintegrates at a lower part of gastrointestinal tract, comprising a compound <A> having a molecular weight of 1,000 or less and having a disulfide bond and a polymer <B> having a molecular weight of above 1,000 and having a property of being decomposed by enterobacteria, and/or a property of being softened, swelled or dissolved due to a decrease in pH, to a formed product comprising such a composition, and to a preparation comprising such a formed product.

BACKGROUND ART

To deliver a drug specifically to a colon in the gastrointestinal tract results in an increased therapeutic effect by local accumulation of the drug upon the treatment of local gastrointestinal tract diseases such as ulcerative colitis and clonal diseases. In such a delivery, because no absorption of the drug occurs before it reaches the colon, side effects attributable to systemic circulation of the drug is decreased and the loss of the drug before it reaches the site where it is effective can be prevented.

Expecting these, many reports have been made on the system that delivers a drug targeting the colon and are roughly classified into the following three groups.

A first group includes a system that releases a drug in response to a change in pH. In the case of a general enteric-coated preparation on which many reports have been made, due to a large biogenic influence of a change in pH in a day in the gastrointestinal tract or of diets, it may occur that the preparation is disintegrated in an upper part of small intestine or on the contrary it is dejected as it is without being disintegrated. Therefore, it cannot be said that colon-specific delivery of a drug is unfailingly realized. Furthermore, a system in which an enteric coating is applied outside acid-soluble coating that is designed to utilize a decrease in pH due to an organic acid produced in the colon is disclosed (JP 10-152431A). However, since disintegration in response to a slight change in pH is required, the system is susceptible to the influence of a change in bacteria flora and the like in the colon and it is difficult to unfailingly deliver a drug colon-specifically.

A second group includes a system that releases a drug time-dependently (JP 7-72130B, JP 7-196477A, EP 0384646B, and JP 7-2650A and 7-10745A). The release sites of them are controlled by time of migration of the preparation in the gastrointestinal tract, so that the release of the drug is greatly susceptible to the biogenic influences of the movement of gastrointestinal tract, of diets or of pathological state. Accordingly, problems arise. In the case where the residence time in the small intestine of the preparation is long, it is disintegrated in the small intestine. In the case where the residence time in the small intestine and large intestine of the preparation is short, it is dejected as it is without being disintegrated. Therefore, it is difficult to unfailingly deliver a drug in a specified region of a lower part of gastrointestinal tract.

A third group includes systems that utilize enterobacteria on which an increasing number of studies have been made in recent years. These systems are roughly classified into two systems. One is a system in which the preparation contains an azo polymer or a disulfide polymer, which is decomposed and disintegrated by the reducing activity of enterobacteria (J. Kopecek et al., Pharmaceutical Research, Vol. 9, No. 12, pages 1540–1545, 1992; Y. Kimura, et al., POLYMER, Vol. 33, No. 24, pages 5294–5299, 1992; and WO91/11175). Another is a system in which the preparation contains a polysaccharide, which is decomposed and disintegrated by the polysaccharide decomposing activity of mainly anaerobic bacteria in the intestine (JP 5-508631A; W. G. Cook, et al., Pharmaceutical Research, Vol. 10, No. 10, S223, 1993).

Reportedly, the reducing activity of the enterobacteria is high, differs only slightly between the species of bacteria, and less influenced by a change in bacterial flora due to a disease or the like (T. Mitsuoka: Metabolism of Enteric Flora, pages 1–17, Academic Printing Center (1988)). However, in the system using an azo polymer or a disulfide polymer thus far disclosed, the decomposition rate of the polymer is low (J. Kopecek, et al., Pharmaceutical Research, Vol. 9, No. 12, pages 1540–1545, 1992). Especially in the case of azo polymer, there is a concern about production of noxious substances derived from the azo bond, so that the problem arises that the system cannot endure a long-term use also in consideration of safety.

The system using a polysaccharide may be considered to have a less severe problem on safety since it uses a substance that has originally been used as dietary fiber. Generally, these substances have the problems. They are decomposed in the colon at low decomposition rates (W. G. Cook, et al., Pharmaceutical Research, Vol. 10, No. 10, S223, 1993). In a state of a disease, their disintegration does not proceed due to a change in enterobacteria flora, especially a decrease in anaerobic bacteria, which are main bacteria that decompose polysaccharides (T. Mitsuoka: Metabolism of Enteric Flora, pages 1–17, Academic Printing Center (1988)).

An example of the system using a polysaccharide is one that uses chitosan. Chitosan, which is a kind of polysaccharide, undergoes decomposition by enterobacteria and is softened or dissolved as a result of a decrease in pH in the colon. Therefore, it is frequently used in a drug delivery system targeting the colon (JP 4-41422A and 4-247026A). However, the activity of enzymes such as chitosanase and lysozyme that decompose chitosan is insufficient in the colon and rather it is considered that the mechanism of disintegration of chitosan system depends on a decrease in pH in the colon. Therefore, the problem arises that the function of the system is strongly influenced by the colonic pH variation in the biogenic condition or the change of enterobacteria flora in a state of disease.

Furthermore, there has been proposed a system called CODES intended to achieve colon-specific drug delivery that avoids the influence of pH variation in the colon and releases the drug in the colon is not by means of time control (WO95/28963). This is a system that contains therein a saccharide that will be metabolized into an organic acid by using enterobacteria in the colon and that is coated with an acid-soluble film that is dissolved with the organic acid. However, this system is also questionable as to whether or not it enables unfailing colon-specific drug delivery.

Therefore, a colon-specific, unfailing and quick drug delivery system that is not influenced by a change or difference in pH in the colon between individuals, uptake of diets or the like or a change of enterobacteria flora has been desired.

DISCLOSURE OF THE INVENTION

An object of the present invention is to provide a system for delivering an objective material selectively to a lower part of gastrointestinal tract, unfailingly and quickly without being influenced by a pH variation or a change of enterobacteria flora. Also, an object of the present invention is to provide a composition for disintegration in lower gastrointestinal tract, a formed product comprising such a composition, and a preparation comprising such a formed product. More particularly, an object of the present invention is to provide a system that orally uptakes a material desired to be delivered to a lower part of the gastrointestinal tract and delivers it selectively to the lower part of gastrointestinal tract. The system has dissolved the above-mentioned problems encountered in the prior art, more specifically the problems of being susceptible to the influences by various factors originating in the biogenic condition, such as a pH variation, a change in enterobacteria flora, or movement of gastrointestinal tract and influence of uptake of diets. Also, an object of the present invention is to provide a composition for disintegration in lower gastrointestinal tract, a formed product comprising such a composition, and a preparation comprising such a formed product. An object of the present invention is to provide a capsule, a film, a sheet or a coating film and so forth as the formed product.

The present inventors have made extensive studies in order to achieve the above-described objects. As a result, they have found that a composition for disintegration in lower gastrointestinal tract, comprising a compound <A> having a molecular weight of 1,000 or less and having a disulfide bond (hereinafter, abbreviated as "compound <A>") and a polymer <B> having a molecular weight of above 1,000 and having a property of being decomposed by enterobacteria, and/or a property of being softened, swelled or dissolved due to a decrease in pH (hereinafter, abbreviated as "polymer <B>") quickly disintegrates in a film disintegration test conducted in a pseudo-enteral environment and that the composition disintegrates selectively at a lower part of the gastrointestinal tract in an animal experiment. The present invention has been completed based on the discovery.

Hereinafter, the present invention will be illustrated.

A first aspect of the present invention provides a composition for disintegration in lower gastrointestinal tract, characterized by containing a compound <A> and a polymer <B>.

A second aspect of the present invention provides a composition for release in lower gastrointestinal tract, characterized in that a domain containing a compound <A> is dispersed in a matrix containing a polymer <B>.

A third aspect of the present invention provides a composition for disintegration in lower gastrointestinal tract, characterized by containing a compound <A>, a polymer <B>, and a substance that controls disintegration rate in lower gastrointestinal tract.

A fourth aspect of the present invention provides a formed product for releasing an active ingredient <C> in lower gastrointestinal tract, comprising a shaped product of the composition for disintegration in lower gastrointestinal tract, characterized by containing a compound <A> and a polymer <B>.

A fifth aspect of the present invention provides a preparation for release in lower gastrointestinal tract, characterized in that a composition for release in lower gastrointestinal tract characterized by containing at least an active ingredient <C>, a compound <A>, and a polymer <B> is coated with an enteric polymer film.

A sixth aspect of the present invention provides a preparation for release in lower gastrointestinal tract, characterized in that a composition containing an active ingredient <C> and a pharmaceutically acceptable carrier is coated with a composition for disintegration in lower gastrointestinal tract characterized by containing a compound <A> and a polymer <B> and further coated with an enteric polymer film.

A seventh aspect of the present invention provides a system for peroral uptake of a material desired to be delivered to lower gastrointestinal tract and selective release in the lower gastrointestinal tract, characterized in that a composition for disintegration in lower gastrointestinal tract characterized by containing a compound <A> and a polymer <B> and an enteric polymer film are used.

An eighth aspect of the present invention provides a system for peroral uptake of a material desired to be delivered to lower gastrointestinal tract and selective release in the lower gastrointestinal tract, characterized in that the material desired to be delivered to the lower gastrointestinal tract is coated with or added to a composition for disintegration in the lower gastrointestinal tract characterized by containing a compound <A> and a polymer <B>, and further coated with an enteric polymer film.

BEST MODE FOR CARRYING OUT THE INVENTION

Figure 1A:
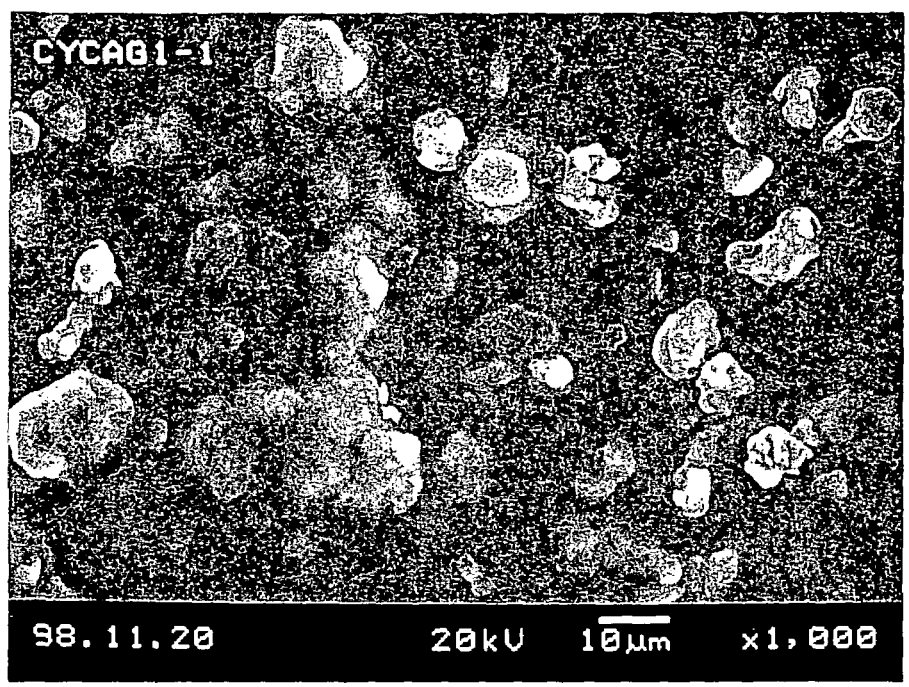
FIG. 1 is a photograph substituting a drawing, showing a surface of a film obtained as a result of Example 1, with (a) showing the state before the test and (b) showing results obtained by use of carbonate buffer.

Hereinafter, the present invention will be illustrated in detail.

First, each component element and terms referred to herein will be explained.

The term "lower gastrointestinal tract" as used herein means ileum and large intestine parts. The term "ileum" refers to a third part of small intestine that continues to duodenum and jejunum. The term "large intestine" means a site toward the site consisting of cecum, colon and rectum. The term "cecum" refers to a blind sack (cul-de-sac) starting from the large intestine and in one end of which the ileum opens. In the lower gastrointestinal tract, enterobacteria increase from the ileum and in the large intestine they inhabit in many kinds and in large numbers.

The term "composition for disintegration in lower gastrointestinal tract" as used herein refers to a functional material that disintegrates selectively in the lower gastrointestinal tract. The "composition for disintegration in lower gastrointestinal tract" of the present invention is characterized by containing a compound <A> and a polymer <B>. It may further contain a substance that controls its disintegrability in the lower gastrointestinal tract. The substance that controls the disintegration rate may be divided into a substance that imparts resistance to disintegration in the small intestine and a substance that accelerates disintegration in the lower gastrointestinal tract.

The "composition for disintegration in lower gastrointestinal tract" of the present invention may be a composition in which the compound <A> and the polymer <B> are mixed uniformly, a composition in which they are contained in a specified order, or a composition in which they are contained completely in disorder and non-uniformly. However, a composition in which the domain that contains the compound <A> is dispersed in a matrix that contains the polymer <B> is preferred. More specifically, a composition in which the particles that contain the compound <A> are uniformly dispersed in a matrix that contains the polymer <B> and is mainly composed of the polymer <B>. The particles that contain the compound <A> are desirably those that are sufficiently small as compared with the film thickness when they are formulated into the "composition for disintegration in lower gastrointestinal tract" and that have narrow particle size distribution.

The term "matrix" as used herein indicates the state where the polymer exists alone or in admixture, integrated into a uniform mixture or composition. The term "domain" refers to the state where a component incompatible with a matrix is dispersed and almost uniformly located in the matrix. The matrix that has domains has different properties from those of simple mixture or simple composition composed of the same components.

The matrix may contain a substance that controls disintegration in lower gastrointestinal tract.

The "compound <A> having a molecular weight of 1,000 or less and having a disulfide bond" used in the present invention has the property that it is decomposed into lower molecular compounds as a result of cleavage of the disulfide bonds due to reduction by enterobacteria so that improvement of water-solubility and/or acidity of the decomposition products is higher than the compound <A>. Such an improvement in water-solubility means that when the composition contains water or contacts water, the particles that contain the compound <A> are dissolved as a result of reduction reaction by enterobacteria. This in turn contributes to formation of micro holes in the film. This accelerates penetration of water in the lumina into the composition of the present invention or causes the enterobacteria to sufficiently penetrate into the composition of the present invention. As a result, the disintegrability of the composition can be increased. On the other hand, an increase in acidity contributes to softening, swelling or dissolution of the specified polymer provided in the present invention. Increased acidity and increased water-solubility simultaneously imparted synergistically contribute to disintegration of film in lower gastrointestinal tract.

The compound <A> includes an oligo peptide that is an amino acid derivative having a disulfide bond, to which cysteine or a peptide containing cysteine is bonded through the disulfide bonds. The compound <A> includes not only naturally deriving ones but also those peptides that can be synthesized from D-form or L-form amino acids. Specific examples of the compound <A> include L-cystine, D-cystine, DL-cystine, diglycyl cystine, cystamine, L-cystinyldiglycine, glutathione disulfide and so forth as the amino acid derivative having a disulfide bond, and thioglycolic acid disulfide (HOOC—R—S—S—COOH/R represents a lower alkylene group) as a synthetic organic low molecule. Cystines (L-cystine, D-cystine, DL-cystine, or any optional mixtures thereof) are more preferable.

The addition amount of the compound <A> is not particularly limited so far as no problem occurs in forming preparations. More specifically, the compound <A> may be contained in the composition of the present invention in a ratio of 1 to 90%. It may be contained in the system of the present invention in a ratio of 1 to 90%. In the formed product of the present invention, it may be contained in a ratio of 1 to 90%. In the case where it is used in the coating film, it is preferred that it be used in a ratio of 10 to 80% in the coating film. The "%" as used herein refers to % of weight per weight and values each based on dry weight.

In the case where it is used in the composition, more particularly formed product or coating film of the present invention, the compound <A> is preferably dispersed in a base material in the state of particles. The reduction by the enterobacteria causes the disulfide bonds to be cleaved and as a result, the compound <A> is decomposed into lower molecular weight compounds to increase the water-solubility of the decomposition products. Upon contact with moisture, a large number of micro holes are formed on the portion where the compound <A> existed in the form of particles. This accelerates penetration of water in the lumina into the composition of the present invention or the enterobacteria sufficiently penetrate into the composition. Therefore, the disintegrability of the composition can be further increased.

The "polymer <B> having a molecular weight of above 1,000 and having a property of being decomposed by enterobacteria, and/or a property of being softened, swelled or dissolved due to a decrease in pH" means a polymer having a molecular weight of above 1,000, having the property of being decomposed by protease, lysozyme and polysaccharidases and so forth of the enterobacteria, having the property of being softened, swelled or dissolved by a decrease in pH, that is, lowering of pH from the vicinity of neutrality to increase acidity, or having the both properties. Simultaneous occurrence of the decomposition by the enterobacteria and softening, swelling or dissolution due to a decrease in pH, the disintegration of the composition containing the polymer <B>, more particularly, coating film in lower gastrointestinal tract proceeds further, so that the material desired to be delivered to the lower gastrointestinal tract can be released more quickly and site-selectively. Therefore, the polymer <B> is preferably a polymer having the property of being decomposed by the enterobacteria and having the property of being softened, swelled or dissolved by a decrease in pH. The molecular weight as used herein refers to an average value, which may be either a number average value or a weight average value.

The polymer <B> can be roughly classified into two groups, i.e., a natural cationic polymer such as chitosan and a synthetic cationic polymer such as acrylic acid-based cationic polymer. Specific examples of the polymer <B> include chitosan as the natural cationic polymer and dimethylaminoethyl methacrylate/methyl methacrylate/butyl methacrylate copolymer (for example, trade name: Eudragit E(Rhoem GmbH, Germany)), polyvinyl acetal diethylaminoacetate (for example, trade name: AEA (Sankyo Company, Limited) and so forth as the synthetic cationic polymer. Natural cationic polymer is preferred, more preferably chitosan may be mentioned.

As the polymer <B>, two or more of the above mentioned polymers may be used in admixture. In this case, a combination of a natural cationic polymer and a synthetic cationic polymer is preferable. Combination of different kinds of polymer can improve the function of the polymer <B>, such as imparting water resistance or controlling disintegration rate. For example, the water resistance can be improved by combining a hydrophobic polymer that is acid soluble and difficult to swell with water as the synthetic cationic polymer.

Chitosan is a deacetylated compound that is obtained by treating chitin contained in large amounts in crustaceans such as crab and lobster with usually a concentrated alkali and completely or partially deacetylating the acetyl groups. It has a linear polysaccharide structure composed of 2-amino-2-deoxy-D-glucose linked through β-1,4 bonds. The chitosan used in the present invention may be any of one having a degree of deacetylation of 40 to 60% by mole, one having a degree of deacetylation of 60% by mole or more and so forth. It is by no means limited by the organism from which it is derived, purification method, and deacetylation method and so forth. To increase disintegrability in the lower gastrointestinal tract, the degree of deacetylation is preferably 60 to 98% by mole.

The polymer <B> may be contained in the composition of the present invention in a ratio of 10 to 99% and may be contained in this system in a ratio of 10 to 99%. In the formed product of the present invention, it may be used in a ratio of 10 to 99%. In the case where it is used in the coating film, it is preferred that it be used in a ratio of 10 to 80% in the coating film. The "%" as used herein is % of weight per weight and values each based on dry weight.

When using the polymers <B> are used in combination, a blending amount ratio of, for example, natural cationic polymer and synthetic cationic polymer may be 99/1 to 1/99. The blending ratio is preferably 99/1 to 30/70 and more preferably 99/1 to 50/50.

In the composition for disintegration in lower gastrointestinal tract according to the present invention, in addition to the above-mentioned components, a substance that controls disintegration rate in lower gastrointestinal tract may be added. The substance that controls the disintegration rate includes a substance for imparting resistance so that the composition will not disintegrate in the small intestine and a substance that accelerates the disintegration of the composition in lower gastrointestinal tract. The substance for imparting resistance to disintegration in the small intestine includes water-insoluble polymer such as ethylcellulose, agar, pectin metal salt, carrageenan, crosslinked polysaccharide or protein, or hydrophobic polymer that is acid soluble and is difficult to be swelled with water, such as dimethylaminoethyl methacrylate/methyl methacrylate/butyl methacrylate copolymer or polyvinyl acetal diethylaminoacetate. The substance that accelerates the disintegration in lower gastrointestinal tract includes polymers such as gelatin, pectin, starch, and cellulose. The substances that control the disintegration rate may be used alone or a combination of two or more of them may be used in the composition for disintegration in lower gastrointestinal tract according to the present invention.

On the other hand, in the case of drugs having high water solubility, it may happen that the drug is leaked as a result of gradual penetration of water in spite of imparting resistance to disintegration. In this case, to prevent the penetration of water, a water-repellent substance such as magnesium stearate may be added to the segment containing the drug or a substance such as a hydrogenated oil may be coated around the segment containing the drug, so that the leakage of the drug can be prevented.

The substance for imparting resistance to the disintegration in the small intestine can prevent swelling or dissolution of polymers, for example, the polymer <B> in the composition in the small intestine. In the case where the substance that accelerates the disintegration in lower gastrointestinal tract is simultaneously added to the composition, decomposition of the composition by gastrointestinal enzymes (for example, digestion of gelatin by protease) can be prevented.

The substance that accelerates the disintegration in lower gastrointestinal tract is a polymer that is decomposed by protease, lysozyme or a polysaccharide-decomposing enzyme of the enterobacteria and can accelerate disintegration of the composition.

The addition amount and blending ratio of the substances that control the disintegration rate in lower gastrointestinal tract may greatly differ depending on the composition for disintegration in lower gastrointestinal tract according to the present invention and form thereof.

The substance for imparting resistance to the disintegration in the small intestine may be contained in the composition of the present invention in a ratio of 0.1 to 80%. In the formed product, it may be used in a ratio of preferably 0.1 to 80%. In the coating film, it may be used in a ratio of preferably 0.1 to 70%. The substance that accelerates the disintegration in lower gastrointestinal tract may be contained in the composition of the present invention in a ratio of 0.1 to 80%. In the formed product, it may be used in a ratio of preferably 0.1 to 80%. In the coating film, it may be used in a ratio of preferably 0.1 to 70%. The "%" as used herein is % of weight per weight and values each based on dry weight.

The method for producing the composition for disintegration in lower gastrointestinal tract according to the present invention includes, for example, a method in which a suspension containing the compound <A> and a solution containing the polymer <B> are mixed and dried, a method in which the compound <A> is dispersed in a solution containing the compound <B> and dried, and a method in which the compound <A> and the polymer <B> are mixed, a suitable solvent is added thereto to dissolve the polymer <B> therein, and the mixture is made uniform and then dried.

Furthermore, to the composition for disintegration in lower gastrointestinal tract may be added a substance for controlling its disintegration rate. In that case, the method for the addition includes a method in which a solution or suspension obtained by dissolving or suspending a substance for controlling disintegration rate in a suitable solvent with optional heating, a suspension containing the compound <A>, and a solution containing the polymer <B> are mixed optionally under the condition of heating and then dried, a method in which a suspension of the compound <A> and a solution of the polymer <B> are mixed with a solution or suspension obtained by dissolving with heating or suspending the substance for controlling disintegration rate optionally under heating conditions and the mixture is dried, a method in which the compound <A>, the polymer <B> and the substance for controlling disintegration rate are mixed, a suitable solvent is added to dissolve or suspend the polymer <B> and the substance for controlling disintegration rate with optional heating, and the mixture is made uniform and dried, and so forth. The solvent used for the production is water or acid solution that is pharmaceutically usable.

Upon drying the composition of the present invention, the drying is performed by natural drying or by blowing under heating. For example, the composition is dried while spraying or it is coated on an objective product and dried. Also, for example, if the composition contains a thermoplastic substance, the composition is cooled and solidified before it can be dried. At the time of production, it is important to take the following into consideration. That is, during the drying or after the drying, (1) in the case where a volatile acid is used in the production process, humidification treatment increases the efficiency of removing the acid, (2) the efficiency of drying can be increased by suitably using an organic solvent, and so forth.

In these production methods, a substance that is desired to be delivered to lower gastrointestinal tract may be added before drying.

A formed product or article can be obtained by forming the composition for disintegration in lower gastrointestinal tract into a suitable form at the time of the drying by the above-mentioned method. By use of a suitable mold at the time of drying the formed product, the composition may be formed into various forms such as a needle, a rod, microfine particles, a sponge, a ring and so forth. The formed products of the present invention are those that can be formed by wet forming such as a capsule, a film, a sheet, a coating film for use in preparation, fiber, a rod-like product, granules, powder, and so forth for containing the active ingredient. Also, the formed products of the present invention include processed products of these, that is, non-woven fabric sheet, woven or knitted fabric, flocks, and coatings on other materials.

In the present invention, the compound <A> can be used in a state of powder, suspension (including particulates suspension) or solution. The powder containing the compound <A> is preferably adjusted so as to have a suitable particle size by, for example, a ball mill before it can be used. The particles that contain the compound <A> are used at a particle size of 100 µm or less and more preferably 50 µm or less. When in use in the composition for disintegration in lower gastrointestinal tract according to the present invention, chitosan as the compound <B> may be used after being dissolved in a dilute acid solution. In the case where chitosan is used after being dissolved, the solvent for chitosan may include solutions of hydrochloric acid, acetic acid, lactic acid, citric acid, malic acid, tartaric acid, glutamic acid, aspartic acid and the like. However, in the case where the acid is removed by the humidification treatment as described above, it is preferable to use acetic acid that is a volatile acid. It is preferred that the blending weight ratio of the acid and chitosan is 30/70 to 99/1. The concentration of the chitosan solution is not particularly limited as far as it has a viscosity that allows production. However, it is preferable that the chitosan solution has a viscosity of 1 to 1,000 cps as a 1% by weight solution (1% acetic acid). To adjust the viscosity of the chitosan solution, chitosan solutions of different viscosities may be mixed and their mixing ratio may be set optionally. Degree of deacetylation and viscosity may be set optionally in combination.

In the case where a synthetic cationic polymer is used as the compound <B>, it may be used by dissolving it in a water-soluble organic solvent such as alcohol or acetone or a water-insoluble organic solvent such as chloroform, methylene chloride, or ethyl acetate, besides the acids.

In the case where chitosan and synthetic cationic polymer are used in combination, they may be dissolved in an acid solution or after dissolving chitosan in an acid solution, a solution of a synthetic cationic polymer in a water-soluble organic solvent may be added thereto. The water-soluble organic solvent includes preferably lower alcohols such as methanol, ethanol, and isopropanol and acetone. If the addition amount of the water-soluble organic solvent is too high, chitosan is precipitated, so that the ratio of the water-soluble organic solvent to the acid solution is preferably 1/99 to 50/50.

The formed product for releasing the contents selectively in lower gastrointestinal tract, comprising a formed of the composition for disintegration in lower gastrointestinal tract characterized by comprising the polymer <A> and the polymer <B> as described herein will be explained.

The formed product has mainly the following forms (1), (2) and (3). (1) includes a sealed vessel-like form for isolating the contents from the outer environment. This is, for example, the case where powdery or granular contents are sealed. Typical example of such includes a capsule. (2) includes a form that envelops the contents. For example, a film that coats tablets or granules or a soft capsule that contains a liquid content and so forth may be mentioned. Typical examples thereof include a film, a sheet or a coating film used for preparations and so forth. (3) includes the case where the contents are contained simultaneously, for example the case where the formed product contains the contents.

The function of the formed product is as follows. After it is moved to the lower gastrointestinal tract, holes are formed in the formed product as triggered by the reduction reaction by the enterobacteria flora increasing in the lower gastrointestinal tract, so that the contents are penetrated therethrough or the formed product is disintegrated, thereby releasing the contents to the outside site-selectively in the gastrointestinal tract.

More particularly, the compound <A> that exists on the surface of the formed product is decomposed relatively quickly, which increases water-solubility of the decomposed product and/or makes the acidity of the decomposed product stronger than that of the compound <A>. As a result, microfine holes are formed in the formed product containing the compound <A> and the polymer <B>. This accelerates penetration of water in the lumina therein or serves for sufficient penetration of enterobacteria to increase disintegrability of the polymer <B>. That is, the polymer <B> is decomposed by the enterobacteria and/or softened, swelled or dissolved. That is, as a result of formation of a large number of microfine holes in the portion where the compound <A> was present, the polymer <B> is decomposed by the enterobacteria and/or softened, swelled or dissolved due to a decrease in pH. On this occasion, preferably the effect of decomposition by enterobacteria and the effect of softening, swelling or dissolving due to a decrease in pH simultaneously take place and the formed product is disintegrated more quickly and at a more high rate to release the contents to the outside.

The formed product preferably is a) a formed product for releasing a content in lower gastrointestinal tract, comprising a formed product of a composition for disintegration in lower gastrointestinal tract characterized by containing the compound <A> and the polymer <B>, b) a formed product for releasing a content in lower gastrointestinal tract, comprising a formed product of a composition for disintegration in lower gastrointestinal tract characterized by containing the compound <A>, the polymer <B> and a substance that controls disintegration rate of the composition in lower gastrointestinal tract, c) a formed product for releasing a content in lower gastrointestinal tract, comprising a formed product of a composition for disintegration in lower gastrointestinal tract characterized by dispersing a domain that contains the compound <A> in a matrix containing the polymer <B> in the formed product, or d) a formed product for releasing a content in lower gastrointestinal tract, comprising a formed product of a composition for disintegration in lower gastrointestinal tract characterized by containing in the formed product a domain that contains the compound <A>, at least the polymer <B> and a substance that controls disintegration rate of the composition in lower gastrointestinal tract.

The polymer <B> used in the formed products may be used alone or in combination as described above.

The term "formed product" means a material obtained by forming the composition for disintegration in lower gastrointestinal tract into a suitable form. The formed product includes formed materials such as a capsule, a film, a sheet, a coating film for use in preparation, fiber, a rod-like product, granules, and powder, and so forth for containing the active ingredient. Further, the formed product includes a material obtained by coating a composition containing a material desired to be delivered to a lower gastrointestinal tract with a composition for disintegration in lower gastrointestinal tract.

When drying the formed products of the present invention, the drying is performed by natural drying or by blowing under heating. For example, the composition is dried while spraying or it is coated on an objective product and dried. Also, for example, if the composition contains a thermoplastic substance, the composition is cooled and solidified before it can be dried. At the time of production, it is important to take the following into consideration. That is, during the drying or after the drying, (1) in the case where a volatile acid is used in the production process, humidification treatment increases the efficiency of removing the acid, (2) the efficiency of drying can be increased by suitably using an organic solvent, and so forth.

The method for coating the composition for disintegration in lower gastrointestinal tract in particular when forming a formed product includes a method of spraying a solution containing the polymer <B> in which the compound <A> is uniformly dispersed and drying, as prepared by the above-mentioned method, a method of dipping a material to be coated in a solution containing the polymer <B> in which the compound <A> is uniformly dispersed, as prepared by the above-mentioned method, and then drawing it out and drying it, and a method of enveloping by a method for producing a soft capsule.

In the case where the coating of formed product or article is performed by spraying and drying the surface of tablets, capsule and granules, the coating may be performed by use of a method in which the preparation is preliminarily stirred in an apparatus such as coating pan or the like in the case of a tablet and a capsule or a fluidized bed granulator or a rolling layer granulator in the case of granules, and a solution obtained by uniformly dispersing the compound <A> in a solution containing the polymer <B> is sprayed to the preparation through a spray nozzle and dried.

In the case where the coating of the formed product is performed by dipping the material to be coated, which is used mainly for coating the surface of a hard capsule, the coating is possible by use of a method in which a hard capsule is molded with a molding pin and dried, and then it is dipped in a solution obtained by uniformly dispersing the compound <A> in a solution containing the polymer <B> and dried. Also, a hard capsule may be produced by directly dipping the molding pin in a solution obtained by uniformly dispersing the compound <A> in a solution containing the polymer <B> and then drawing it out and drying it.

Upon coating the hard capsule, it is preferred that seal treatment be practiced in advance in order to completely coat the bonded portion.

After performing the coating and drying, humidification treatment is optionally performed to remove the acid in the coating, so that the resistance in the small intestine can be increased.

For example, in the case where chitosan is a component, humidification for removing a volatile acid can be performed, for example, under the conditions of 30 to 40° C. and relative humidity of 60 to 75% for a treating time on the order of 24 to 100 hours.

A soft capsule can be produced by adding cystine as the compound <A>, chitosan as the polymer <B>, agar as the water-insoluble polymer, gelatin as the polymer for accelerating disintegration in lower gastrointestinal tract, and so forth as film forming components and using an ordinary method such as a rotary die method or a drip in oil method (seamless method).

Upon producing a soft capsule, it is desirable to add a thermoplastic substance, for example, agar besides the compound <A> and the polymer <B> in order to impart resistance in small intestine. Further, in order to control disintegration in lower gastrointestinal tract, it is desirable to add a thermoplastic substance, for example, agar or gelatin besides the compound <A> and the polymer <B>.

A specific production method for a seamless soft capsule is illustrated hereinbelow. Cystine is dispersed in a solution obtained by adding water to agar and heating the mixture for dissolution, and further gelatin is added thereto and dissolved. Then, a chitosan solution separately dissolved by addition of an acid is added and made uniform suspension. This is used as a film forming liquid. The temperature of the film forming liquid is preferably 80° C. or less and more preferably 70° C. or less, in order to prevent the degradation of the components. The viscosity of the film forming liquid is 300 cps or less, and more preferably 250 cps or less, at 70° C. The content liquid is produced by dissolving or suspending a drug in an oil or fat or emulsifying an aqueous solution of a drug with oil or fat. In the case where a triple nozzle is used as described above, the aqueous solution as it is may be used as the content solution. A content solution is discharged from inside of a double or triple nozzle and a film forming liquid is discharged from outside thereof into the oil liquid each by use of a metering pump at a constant rate, and the discharged liquid is cut at a constant interval by means of a certain type of a physical force such as oscillation, impact, a difference in discharge rate between the capsule liquid and oil liquid to thereby produce spherical seamless soft capsules of 0.1 to 20 mm in diameter through a surface tension between the oil liquid and film forming liquid.

What is described above mainly illustrates an example applied to the seamless soft capsule of the present invention. However, the present invention is also applicable to a hard capsule, a rotary die capsule, and other soft capsules.

In the case where the formed product of the present invention is a formed product composed of the compound <A> and the polymer <B>, it is desirable that it be treated with an alkali or a water-soluble alcohol-based organic solvent, or subjected to humidification treatment in order to impart resistance thereto so as not to disintegrate in the small intestine.

The system of the present invention is a system prepared by use of the composition for disintegration in lower gastrointestinal tract characterized by containing the compound <A> and the polymer <B> and an enteric polymer film, for orally uptake of a material desired to be delivered to the lower gastrointestinal tract (for example, active ingredient <C> or bacteria cell such as bifido bacteria or the like) and for the release of it selectively in lower gastrointestinal tract.

Further, the system of the present invention, which may be either coated with the composition for disintegration in lower gastrointestinal tract or contained in the composition, is preferably further coated with an enteric polymer film. Furthermore, the composition for disintegration in lower gastrointestinal tract used in the system of the present invention is preferably a dispersion of a domain containing the compound <A> in a matrix containing the polymer <B>.

The polymer <B> used in the system of the present invention may be used alone or in combination as described above.

The system of the present invention includes not only a preparation that comprises composition for disintegration in lower gastrointestinal tract, more particularly a formed product using the composition, and an enteric polymer film and releases the active ingredient <C> selectively in lower gastrointestinal tract but also a sustained release preparation, a diagnostic method and a material for use therein, and a functional food and so forth. For example, the system of the present invention includes the preparations having the above-mentioned features as main modes but is not limited to these modes and includes its use in a pulsatile release type sustained preparation as one mode of the system of the present invention. That is, by combining the preparation for release in lower gastrointestinal tract as a slow release unit with a quick release unit, there can be obtained a sustained release preparation of which the unit that releases a drug in, for example, the stomach and small intestine disintegrates in series and thereafter the unit that releases a drug in lower gastrointestinal tract disintegrates. Thus, the system of the present invention can be applied to various drugs of which sustained release is desired.

Another mode of the system of the present invention finds application not only in the field of treatment but also in the field of diagnostics. For example, a capsule containing a drug such as a contrasting agent can be used in combination with X-ray and an NMR image forming technique by allowing the drug to be released in lower gastrointestinal tract after taking the capsule. In other fields of diagnostics, a would-be antigen (allergen) or allergic food component can be delivered to lower gastrointestinal tract for the diagnostics of allergy. Furthermore, in another mode, the system of the present invention includes a functional food. For example, filling bifido bacteria or a substance that has an activity of growing bifido bacteria (example; oligosaccharide and so forth) or the like is in a capsule and allowing it to be released selectively in lower gastrointestinal tract, the bifido bacteria in the lower gastrointestinal tract can be increased and the activity of recovering intestinal order can be utilized.

The "preparation for release in lower gastrointestinal tract" of the present invention is a preparation for release in lower gastrointestinal tract characterized in that the composition for disintegration in lower gastrointestinal tract characterized by containing at least the active ingredient <C>, the compound <A> and the polymer <B> is coated with an enteric polymer film. It is a preparation that has a function of selectively releasing the active ingredient <C> in lower gastrointestinal tract by use of the "composition for disintegration in lower gastrointestinal tract" of the present invention, which is a functional material that disintegrates selectively in lower gastrointestinal tract, and further by used of an enteric polymer film.

The preparation of the present invention is preferably composed of a composition containing the active ingredient <C> and a pharmaceutically acceptable carrier, and coated with the composition for disintegration in lower gastrointestinal tract characterized by containing the compound <A> and the polymer <B> and further with an enteric polymer film. Further, in the system of the present invention, the composition for disintegration in lower gastrointestinal tract used is preferably one in which the domain containing the compound <A> is dispersed in the matrix containing the polymer <B>.

In the preparation for release in lower gastrointestinal tract of the present invention, the polymer <B> may be used alone or in combination as described above.

The form of the preparation for release in lower gastrointestinal tract of the present invention includes a tablet, a granule, a fine granule, a powder, a capsule, and so forth, and any form may be adopted. For example, in the case of a tablet, a compression formed tablet containing an active ingredient may be coated with a film of the composition of the present invention. In particular, in order to quickly disperse a drug having a very high fat solubility, such as steroid, in an environment where there is a small amount of water, such as colon, a form of capsule having filled therein a drug in a state of solution or suspension is preferred. The form of a soft capsule is more preferred in consideration of production costs. The drug that can be encapsulated by a soft capsule generally includes drugs having high fat solubility that is readily soluble in oil or fat. In the case of water-soluble drugs, the encapsulation can be practiced by a method of suspending the drug in oil or fat. In the case where a water-soluble drug is filled in a seamless capsule, besides the method of suspending a drug in oil or fat, a method in which a triple nozzle is used and an oil or fat layer is arranged between an aqueous solution of the drug and a film may be practiced (JP 8-10313 A). The preparation of various kinds may be produced by one having ordinary skill in the art.

The material desired to be delivered to lower gastrointestinal tract, which the objective material in the present invention, is not particularly limited.

In the case where the system of the present invention is used as a functional food, it includes, for example, lactic acid bacteria preparations such as lactomine preparations, bifido bacteria-lactomin compound, butyric acid bacteria, or resistant lactic acid bacteria, lactose decomposing enzyme drugs such as β-galactosidase and tilactase, vitamins and so forth.

In the case where the system of the present invention is used for diagnosis, it includes chemicals for a contrasting agent, such as amidotrizoic acid or barium sulfate. It is used in combination with X-ray and NMR image forming technology by taking a capsule encapsulating it therein. It also includes antigens (allergens such as egg, milk, soybean, wheat, peanut, buckwheat, and banana), allergic food components (drug contained in food, colorant, preservative, yeast, bacteria and so forth) and the like for the diagnosis of allergy. It is released in lower gastrointestinal tract when in use.

In the case where the system of the present invention as a medical (animal medical) preparation, the "material desired to be delivered to lower gastrointestinal tract" is as explained in "active ingredient <C>". The following (1) to (4) may be mentioned of.

(1) Therapeutic drugs of which site-specific delivery is desirable include drugs considered to be effective to diseases in lower gastrointestinal tract, for example, therapeutical drugs for Crohn's disease, ulcerative colonitis, colon cancer and the like. Specific examples thereof include 5-ASA derivatives such as mesalazine, 5-aminosalycilic acid (5-ASA), and salazosulfapyridine, steroids such as cortisone acetate, triamcinolone, dexamethasone, hydrocortisone, prednisolone, betamethasone, betamethasone valerate, paramethasone acetate, fludrocortison acetate, halopredone acetate, fluocinolone acetonide, fluocinonide, and hydrocortisone acetate, antedrug type steroids such as budesonide, beclometasone dipropionate, fluticason propionate, and betamethazon dipropionate.

Immunosuppressors such as cyclosporin, 6-mercaptopurine, tacrolimus, azathioprine, and mizoribine, protease inhibitors such as ulinastatin and camostat mesilate, highly unsaturated fatty acids such as EPA and DHA and esters thereof, anticancer agents such as tegafur, fluorouracil and bleomycin, Antirheumatic agents such as sodium aurothiomalate, penicillamine, auranofin, disodium lonzarit, and actariot, antathmatic agents such as beclometazone propionate, hemostats such as carbazochrom sodium sulfonate, adrenochrome guanylhydrazone mesilate, ethanesylate, ε- aminocaproic acid, tranexamic acid, thrombin, cellulose chloride, gelatin, monoethanolamine oleate, and polycazole, fungicides such as amphotericin B, flucytocine, miconazole, fluconazole, itraconazole, and griseofulvin, various antibiotics such as β-lactams (penicillins, cephems), amino glucosides, macrolides, tetracyclines, new quinolones, vancomycin, and clindamycin, anti-inflammatory agents such as salicylic acids (sodium salicylate, aspirin, sazapirin, etc.), aryl acetates (diclofenac sodium, tolmethine sodium, fenbufen, indomethacin, amfenac sodium, mebumethone, etc.), propionic acids (ibuprofen, ketoprofen, naproxene, loxoprofen sodium, etc.), fenamic acids (flufenamic acid, mefenamic acid, floctafenin, tolfenamic acid, etc.), pyrazolones (ketophenylbutazone, etc.), and oxicams (piroxicam, ampiroxicam, etc.), local anesthetics such as procaine hydrochloride, oxyprocaine hydrochloride, ethyl aminobenzoate, cocaine hydrochloride, tetracaine hydrochloride, lidocaine hydrochloride, dibucaine hydrochloride, protocaine hydrochloride, and oxazane, enterokinesis accelerators such as cisapride.

(2) The material desired to be delivered to lower gastrointestinal tract directly includes, for example, a laxative and an antidiarrhetic. It is desirable that these be released selectively in the colon. Specific examples of cathartics include large intestine stimulating cathartics, for example, anthraquinone derivatives contained in galenicals such as senna, rhubarb and aloe, phenolphthalein derivatives such as phenovaline, diphenyl derivatives such as laxoberon, large intestine stimulating cathartics such as bisacodyl, and small intestine stimulating cathartics such as castor oil and olive oil, and so forth. Specific examples of antidiarrhetics include astringents such as albumin tannate and bismuth formulations, bactericides such as berberine chloride and berberine chloride arranged formulations, enterokinesis inhibitors such as opium alkaloid, mepenzolate bromide (parasympatholytic drug/cholinolytic drug), loperamide chloride, trimebutine maleate, oxethazaine, tiquizium bromide, and cisapride.

(3) Also a drug that could cause gastrointestinal injury in upper gastrointestinal tract due to its direct action to the gastric wall, for example, a nonsteroidal anti-inflammatory drug (NSAID) can be released selectively in lower gastrointestinal tract and allowed to be absorbed thereby. Specific examples thereof include salicylic acids (sodium salicylate, aspirin, sazapirin, etc.), aryl acetates (diclofenac sodium, trimethine sodium, fenbufen, indomethacine, amfenac sodium, mebutone, etc.), propionic acids (ibuprofen, ketoprofen, naproxen, loxoprofen sodium, etc.), fenamic acids (flufenamic acid, mefenamic acid, floctafenine, trifenamic acid, etc.), pyrazolones (ketophenylbutazone, etc.), oxicams (piroxicam, ampiroxicam, etc.) and the like anti-inflammatory agents.

(4) Various physiologically active polypeptides, proteins and derivatives thereof of which decomposition in upper gastrointestinal tract (peptide), in particular decomposition in upper gastrointestinal tract have to be inhibited, for example, insulin, calcitonin, angiotensin, vasopressin, desmopressin, LH-RH (luteinizing hormone-releasing hormone), somatostatin, glucagon, oxytocin, gastrin, cyclosporin, somatomedin, secretin, h-ANP (human atrial sodium diuretic peptide), ACTH (adrenocorticotropic hormone), MSH (melanophore stimulating hormone), β-endorphin, muramyl dipeptide, enkephalin, neurotensin, pombesin, VIP (vasoactive intestinal polypeptide), CCK-8 (cholecystokinin-8), PTH (parathyroid hormone), CGRP (calcitonin gene related peptide), TRH (thytropin releasing hormone), endothelin, hGH (human growth hormone), and cytokines such as interluekins, interferons (α, β and γ), colony stimulating factor, and tumor necrosis factor, and derivatives thereof. The peptides and proteins include not only those derived from natural substances but also pharmacologically active derivatives and analogues thereof (for example, mutants with deletion, substitution or addition by genetic recombination). Therefore, calcitonin, which is an objective in the present invention includes not only naturally occurring products such as salmon calcitonin, human calcitonin, porcine calcitonin, eel calcitonin, and chicken calcitonin but also analogues thereof such as [Asul, 7]-eel calcitonin (elcatonin). Insulin not only includes human insulin, porcine insulin, and eel insulin but also includes their analogues such as their genetic recombinants.

In the present invention, the material desired to be delivered in lower gastrointestinal tract may be used alone or as mixtures of two or more of them, or may be mixed with pharmaceutically acceptable carriers.

Further, drugs that have high first pass effects when they are absorbed in the small intestine or that have decreased bioavailability because of inhibited absorption due to the interaction with undigested food or components of gastrointestinal juice in the small intestine are preferred examples of the active ingredient of the present invention. The drugs that are influenced by the drug-metabolizing enzyme in the upper gastrointestinal tract when absorbed in the small intestine are preferred examples of drugs that are released and absorbed in the rectum portion of the large intestine.

The materials that are desired to be delivered to the lower gastrointestinal tract may be optionally mixed with other additives that have been accepted as drug additives and food additives, or may be contained in an oil base.

The "enteric polymer film" is an enteric film made from a polymer that is soluble in a liquid at a pH 5 or more as a base material. It is not particularly limited as far as it is selected from various enteric base materials that can impart resistance to gastric juice when they are used in the preparation of the present invention and that have been widely used conventionally. In the system of the present invention, it is preferred that an enteric film is provided on the outermost layer in order to protect the polymer that is dissolved in an acidic state from the low pH environment in the stomach. Specific examples of the base material used for such an enteric coating film include anionic acrylic resins such as methacrylic acid/methyl acrylate copolymer and methacrylic acid/ethyl acrylate copolymer (for example, Eudragit L, Eudragit S (both trade names; Roehm, Germany), etc.), hydroxypropylmethylcellulose acetate succinate (HPMCAS), hydroxypropylmethylcellulose phthalate (HPMCP), cellulose acetate phtalate (CAP), hydroxypropylmethylcellulose (HPMC), carboxymethylcellulose acetate phthalate (CMCAP), shellac, and so forth. Mixtures of these may also be used. The enteric coating film may be used by coating to form a film layer in an ordinary method. Also, it may be used in the form of a capsule produced using the base material. That is, a soft capsule using the composition for disintegration in lower gastrointestinal tract containing at least the compound <A> and the polymer <B> according to the present invention, which is a constituent unit for releasing the active ingredient in lower gastrointestinal tract, may be placed in a capsule of an enteric coating film before it can be used.

The term "coated" as used herein includes not only the state of being coated to form a coating film but also the state of being placed in, for example, the capsule that is made with the polymers as described above.

In the system of the present invention, one or more pharmaceutically acceptable additives may be added in order to facilitate its absorption or dispersion in the lower gastrointestinal tract. Such an additive includes oil or fat, a surfactant, a medium chain aliphatic carboxylic acid and its salt, EDTA, and various protease inhibitors for preventing enzymatic decomposition in the colon in the case of absorption of peptide or the like. Examples of the oil or fat include medium chain fatty acid triglycerides (migliore, etc.), hard fat (Witep sol, etc.), and vegetable oil (olive oil, etc.). The surfactant includes, for example, various bile acid salts, sodium lauryl sulfate, sucrose fatty acid esters, sorbitan fatty acid esters, polyoxysorbitan fatty acid esters (Tween 80, etc.), polyoxyethylene hardened castor oil (HCO60, etc.), polyoxyethylene lauryl ether, polyethylene glycol fatty acid ester and/or mixtures of these with glyceride (for example, trade name; GELSIE (Gatefoce, France), and so forth. The medium chain aliphatic carboxylic acid includes caproic acid, caprylic acid, capric acid, lauric acid, myristic acid, and so forth. Their salts are typically sodium salts and potassium salts. The protease inhibitor includes aprotinin, ulinastin, camostat mesilate and so forth.

Particularly preferable combinations of constituent elements of the composition for disintegration in lower gastrointestinal tract, formed product using the composition, preparation or system for release in lower gastrointestinal tract using them will be described hereinbelow. However, the present invention should not be construed as being limited thereto.

Particularly preferred examples of the composition for disintegration in lower gastrointestinal tract include a) a composition for disintegration in lower gastrointestinal tract characterized by containing cystine and at least chitosan, b) a composition for disintegration in lower gastrointestinal tract characterized by containing cystine and at least chitosan and a substance that controls disintegration rate in lower gastrointestinal tract, c) a composition for disintegration in lower gastrointestinal tract characterized in that a domain containing cystine is dispersed in a matrix containing at least chitosan, and d) a composition for disintegration in lower gastrointestinal tract characterized in that a domain containing cystine is dispersed in a matrix containing at least chitosan and a substance that controls disintegration rate in lower gastrointestinal tract.

Particularly preferred examples of the formed product include a) a formed product for releasing a content in lower gastrointestinal tract, comprising a formed product of the composition for disintegration in lower gastrointestinal tract characterized by containing cystine and at least chitosan, b) a formed product for releasing a content in lower gastrointestinal tract, comprising a formed product of composition for disintegration in lower gastrointestinal tract characterized by containing cystine and at least chitosan and a substance that controls disintegration rate in lower gastrointestinal tract, c) a formed product for releasing a content in lower gastrointestinal tract, comprising a formed product of composition for disintegration in lower gastrointestinal tract characterized in that a domain containing cystine in the formed product is dispersed in a matrix containing at least chitosan, and d) a formed product for releasing a content in lower gastrointestinal tract, comprising a formed product of composition for disintegration in lower gastrointestinal tract characterized in that a domain containing cystine in the formed product is dispersed in a matrix containing at least chitosan and a substance that controls disintegration rate in lower gastrointestinal tract.

Particularly preferred examples of the preparation include i) a preparation for release in lower gastrointestinal tract characterized in that a composition for release in lower gastrointestinal tract characterized by containing cystine and at least chitosan and an active ingredient <C> are coated with an enteric polymer film, ii) a preparation for release in lower gastrointestinal tract characterized in that a composition containing an active ingredient <C> and a pharmaceutically acceptable carrier is coated with a composition for disintegration in lower gastrointestinal tract characterized by containing cystine and at least chitosan and further coated with an enteric polymer film, and iii) a preparation for release in lower gastrointestinal tract characterized in that a composition containing an active ingredient <C> and a pharmaceutically acceptable carrier is coated with a composition for disintegration in lower gastrointestinal tract characterized in that a domain containing cystine in the composition is dispersed in a matrix containing cystine and at least chitosan and further coated with an enteric polymer film.

Particularly preferred examples of the system include i) a system for peroral uptake of a material desired to be delivered to lower gastrointestinal tract and selective release in the lower gastrointestinal tract, characterized in that a composition for disintegration in lower gastrointestinal tract characterized by containing cystine and at least chitosan and an enteric polymer film are used, ii) a system for peroral uptake of a material desired to be delivered to lower gastrointestinal tract and selective release in the lower gastrointestinal tract, characterized in that the material desired to be delivered to the lower gastrointestinal tract is coated with or added to a composition for disintegration in the lower gastrointestinal tract characterized by containing cystine and at least chitosan, and further is coated with an enteric polymer film, and iii) a system for peroral uptake of a material desired to be delivered to lower gastrointestinal tract and selective release in the lower gastrointestinal tract, characterized in that a composition containing an active ingredient <C> and a pharmaceutically acceptable carrier is coated with a composition for disintegration in lower gastrointestinal tract characterized in that a domain containing cystine in the composition is dispersed in a matrix containing cystine and at least chitosan and further coated with an enteric polymer film.

The above-mentioned chitosan used in particularly preferred combinations of constituent elements of the composition for disintegration in lower gastrointestinal tract, formed product, preparation for release in lower gastrointestinal tract or system of the present invention may be used alone or in combination as described above. By using a synthetic cationic polymer, for example, an acid-soluble hydrophobic polymer, in combination, swelling of chitosan with water can be inhibited and its water resistance can be increased further.

The compounding weight ratio of cystine to chitosan may be set optionally. However, it is preferred to set it in the range of 10/90 to 90/10. It is preferred that the compounding weight ratio of agar to gelatin be set in the range of 10/90 to 90/10. Further, the total compounding weight of agar and gelatin is preferably 5% or more based on the total weight of the capsule film (% of weight per weight; value on dry basis).

The adaptation diseases targeted by the system for peroral uptake of a material desired to be delivered to lower gastrointestinal tract and selective release in the lower gastrointestinal tract according to the present invention are not particularly limited as far as they are based on the main medicinal effect. The diseases may be coped with by either systemic administration or local administration. The diseases intended to be coped with by local administration include lower gastrointestinal tract diseases (ulcerative colonitis, Crohn's disease, colorectal cancer, colon cancer, colorectal polyps, irritable colonitis, irritable bowel syndrome, etc.). The system of the present invention may be used also as preparations such as an enteral flora-forming agent, a hemorrhoids treating agent, an intestinal disorder treating agent, and a cathartic.

Next, the present invention and effects thereof will be illustrated in more detail with reference to examples and test examples.

EXAMPLE 1

50 ml of water was added to 1 g of agar, 1 g of cystine, and 1 g of glycerol, and the mixture was stirred at 90° C. to dissolve the agar. After the temperature of the resultant suspension was decreased to 70° C., 1.5 g of gelatin was added and the mixture was stirred to dissolve. Further, a solution of 1.5 g of chitosan (Chitosan LL (registered trademark), viscosity (0.5%, 20° C.); 20 cps or more, Yaizu Suisan), and 0.5 g of acetic acid in 25 ml of water was added thereto and stirred to obtain a uniform suspension.

7 ml of this suspension is spread in a dish of 9.3 mm in inner diameter and dried to prepare a cast film (about 60 µm in film thickness).

EXAMPLE 2

50 ml of water was added to 1 g of agar, 1 g of cystine, 1 g of glycerol, and 1 g of corn starch and the mixture was stirred at 90° C. to dissolve the agar and corn starch. Then, the temperature of the resultant suspension was decreased to 70° C. Further, a solution of 1.5 g of chitosan (Chitosan LL (registered trademark), viscosity (0.5%, 20° C.); 20 cps or more, Yaizu Suisan), and 0.5 g of acetic acid in 25 ml of water was added thereto and stirred to obtain a uniform suspension.

7 ml of the suspension was spread in a dish of 9.3 mm in inner diameter and dried to prepare a cast film (about 60 µm in film thickness).

COMPARATIVE EXAMPLE 1

50 ml of water was added to 1 g of agar, 1 g of β-cyclodextrin, 1 g of glycerol, and 1 g of corn starch and the mixture was stirred at 90° C. to dissolve the agar and corn starch. Then, the temperature of the resultant suspension was decreased to 70° C. Further, a solution of 1.5 g of chitosan (Chitosan LL (registered trademark), viscosity (0.5%, 20° C.); 20 cps or more, Yaizu Suisan), and 0.5 g of acetic acid in 25 ml of water was added thereto and stirred to obtain a uniform suspension.

7 ml of the suspension was spread in a dish of 9.3 mm in inner diameter and dried to prepare a cast film (about 60 µm in film thickness).

EXAMPLE 3

100 ml of water was added to 2 g of agar, 8 g of cystine, and 8 g of glycerol, and the mixture was stirred at 90° C. to dissolve the agar. After the temperature of the resultant suspension was decreased to 70° C., 10 g of gelatin was added and the mixture was stirred to dissolve gelatin. Further, a solution of 6 g of chitosan and 6 g of citric acid in 60 ml of water was added thereto and stirred to obtain a uniform suspension. Then seamless soft capsules having a particle size of about 2.4 mm and a weight of about 8.9 mg (content of about 5.3 mg) were produced by a drip in oil method using the suspension as a film forming liquid and a solution (0.25 mg/g) of fat-soluble red dye Sudan IV dissolved in a medium chain fatty acid triglyceride (MCT) as a content liquid. As the chitosan, a 2.8:3.2 mixture of Chitosan LL (registered trademark) (viscosity (0.5%, 20° C.); 20 cps or more, Yaizu Suisan) and Chitosan 100 (registered trademark) (viscosity (0.5%, 20° C.); 90.2 cps, Wako) was used.

EXAMPLE 4

In the same manner as in Example 3, seamless capsules having a particle size of about 2.4 mm and a weight of about 8.7 mg (content of about 5.9 mg) were produced using a suspension (50 mg/g) of indomethacine dispersed in a medium chain fatty acid triglyceride (MCT) as a content liquid.

TEST EXAMPLE 1

The cast films obtained in Examples 1, 2 and comparative Example 1 were placed in a sealed vessel containing a suspension of cecum contents of a Wistar rat (30 g (wet weight) of cecum contents/60 g of pH 6.8 carbonate buffer) or pH 6.8 carbonate buffer to dip therein and the space was purged with carbon dioxide gas. Thereafter, the vessel was sealed and weakly shaken at 37° C. for 16 to 20 hours. After the shaking, the cast films were taken out, washed with water and dried. The surface of each cast film was observed on a scanning electron microscope at a magnification of 1,000 times.

The carbonate buffer was prepared by weighing respective components, dissolving them in a suitable amount of water, making the total amount to 1 liter and bubbling $CO_2$ into the solution to adjust it to pH 6.8.

| | |
|---|---|
| $NaHCO_3$ | 9.240 g |
| $Na_2HPO_4.12H_2O$ | 7.125 g |
| NaCl | 0.470 g |
| KCl | 0.450 g |
| $CaCl_2.2H_2O$ | 0.073 g |
| $MgCl_2.6H_2O$ | 0.087 g |
| $H_2O$ | suitable amount |
| Total amount | 1 liter. |

The cast film in Comparative Example 1 had a smooth surface and no corrosion was observed after dipping it in the suspension of cecum contents. On the contrary, deep corrosion was observed in the cast film of Example 1 and the corrosion further proceeded in the cast film of Example 2. Furthermore, no corrosion was observed in the cast films of Examples 1 and 2 with dipping in the carbonate buffer.

Here, "corrosion" refers to the state where a part of the film is detached from the surface of film due to decomposition or dissolution to form a groove or hole. The results are shown in FIGS. 1 to 4, which are scanning electron micrographs.

Figure 1B:
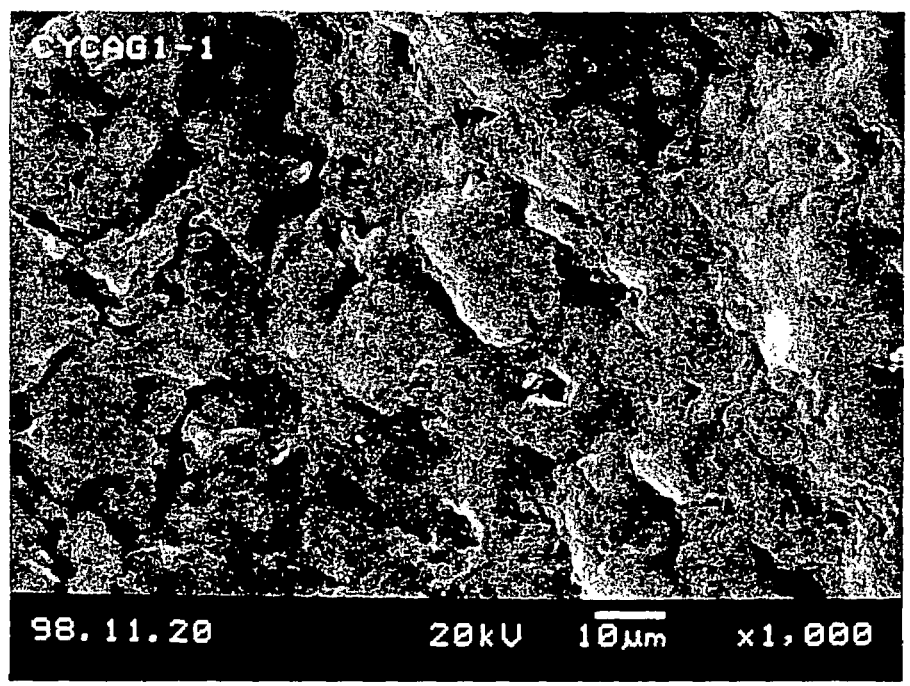
Figure 2:
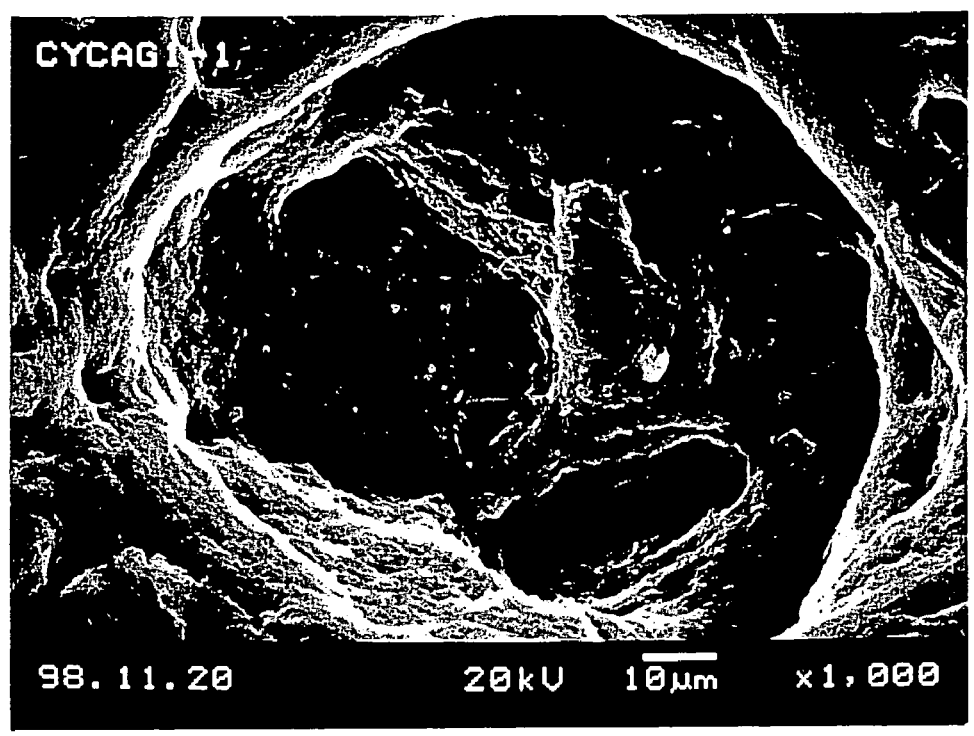
FIG. 2 is a photograph substituting a drawing, showing a surface of a film obtained as a result of Example 1, illustrating results with a suspension of cecum contents.
Figure 3A:
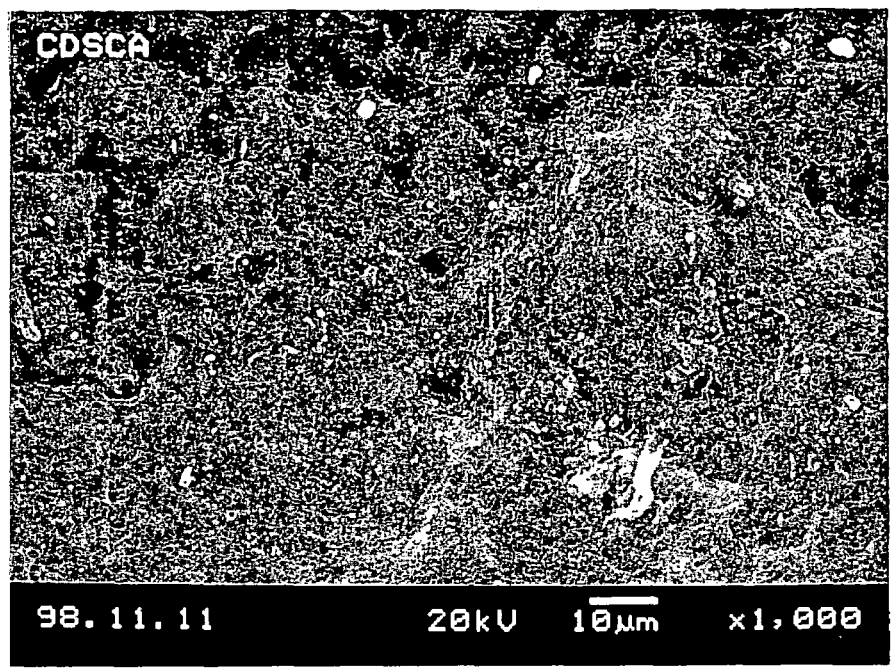
FIG. 3 is a photograph substituting a drawing, showing a surface of a film obtained as a result of Comparative Example 1, with (a) showing the state before the test and (b) showing results obtained by use of carbonate buffer.
Figure 3B:
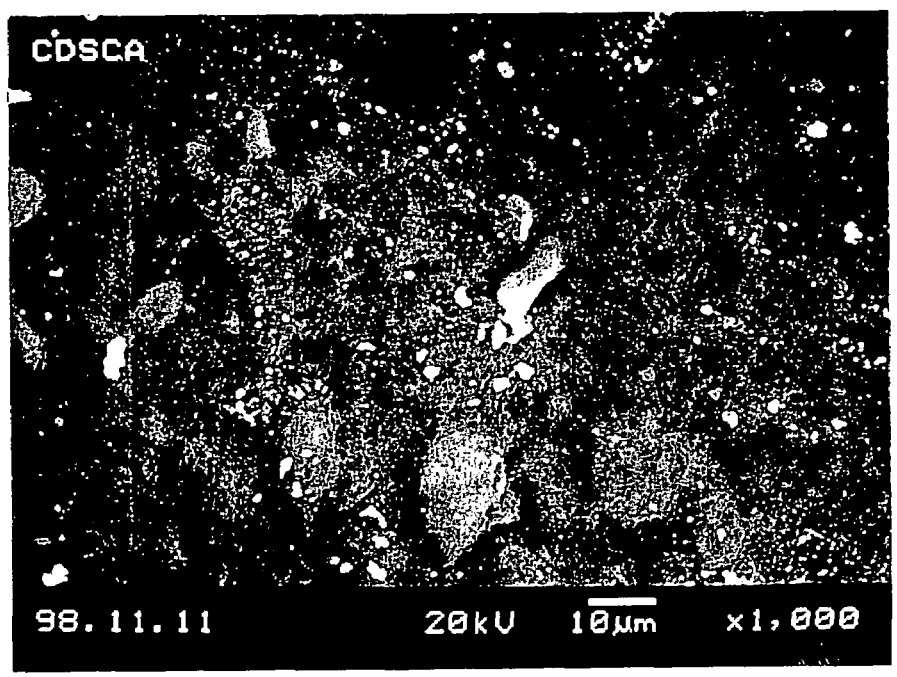
Figure 4:
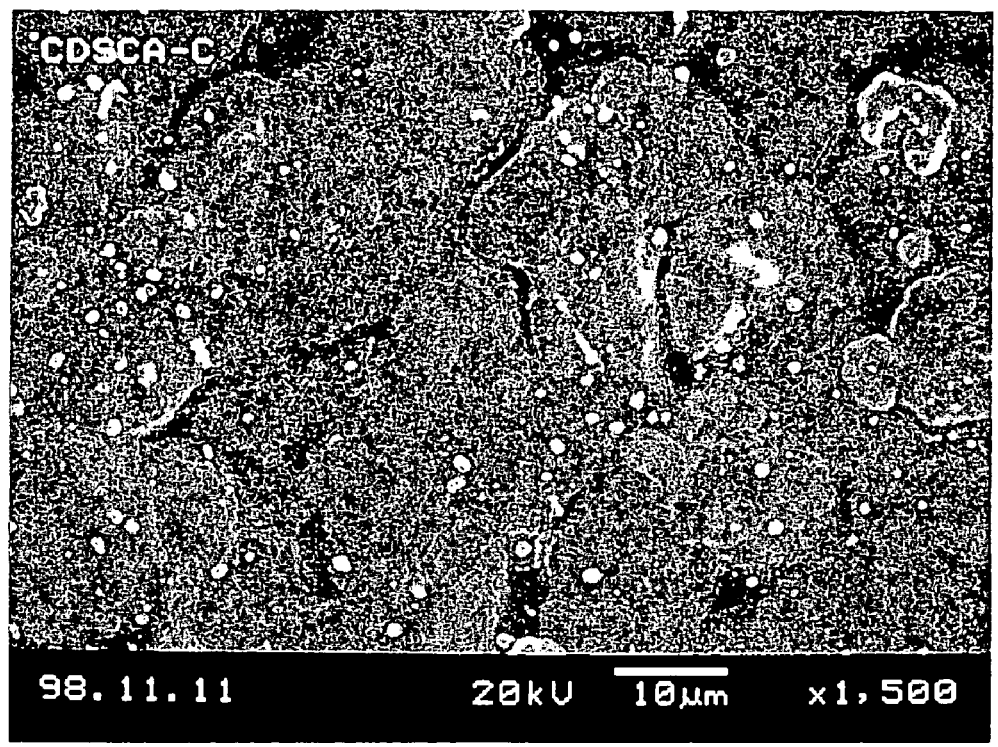
FIG. 4 is a photograph substituting a drawing, showing a surface of a film obtained as a result of Comparative Example 1, illustrating results with a suspension of cecum contents.

FIG. 1(a) The cast film of Example 1
Before the test
FIG. 1(b) Example 1
In carbonate buffer
16 Hours (37° C.)
FIG. 2 Example 1
In suspension of cecum contents
16 Hours (37° C.)
FIG. 3(a) The cast film of Comparative Example 1
Before the test
FIG. 3(b) Comparative Example 1
In carbonate buffer
20 Hours (37° C.)
FIG. 4 Comparative Example 1
In suspension of cecum contents
20 Hours (37° C.)

TEST EXAMPLE 2

Figure 5:
FIG. 5 is a diagram illustrating the chronological state of the seamless capsules in gastrointestinal tract with lapse of time after administration of seamless capsules to a rat (n=3) with fed condition.

Three seamless soft capsules obtained in Example 3 were filled in an enteric capsule (enteric capsule for animals MGS•AS-M type, Freund Sangyo). Enteric capsules thus obtained were orally administered to rats fed to repletion and rats starved for 20 hours, respectively. In the sate of being fed to repletion, the rats were sacrificed with lapse of time for 4 to 24 hours and the capsules in the gastrointestinal tract were observed. The results are shown in FIG. 5.

In the instant test, the capsule when the rats were fed to repletion did not disintegrate and had maintained high strength of the film so that no leakage of the content liquid was observed in the upper gastrointestinal tract to the ileum. Further, high strength of the film was maintained. However, in the cecum and colon, the film strength decreased and disintegration of capsule and leakage of content liquid were observed.

The film strength was measured as follows. The capsule taken out of the gastrointestinal tract was placed in a dish in which Kim-wipe was laid. Then, a probe of a force gauge (MODEL-9500, produced by Aiko Engineering Co., Ltd.) attached to a movable stand was actuated in the vertical direction to push the capsule and maximum load (unit: N) at which the capsule was broken and the content liquid was leaked was recorded. When the film strength was 0.1 N or less, it was judged that the "film strength was decreased". Unchanged seamless soft capsules had a film strength of 0.25 N or more. The blackened seamless soft capsules had a film strength of 0.1 N or less, so that their film strength was decreased.

EXAMPLE 5

480 ml of water was added to 9 g of chitosan (Chitosan PSH (registered trademark) (viscosity (0.5%, 20° C.); 100 cps or more, Yaizu Suisan) to disperse it and then 81 g of acetic acid was slowly added while stirring to dissolve the chitosan.

To this solution was added a solution of 9 g of dimethylaminoethyl methacrylate/methyl methacrylate/butyl methacrylate copolymer (Eudragit E(registered trademark), Roem GmbH, Germany) in 300 g of ethanol and further a suspension of 9 g of cystine in 100 g of water. The mixture was stirred to make it uniform. Thus, a suspension was obtained.

7 ml of he suspension was spread in a dish of 9.3 mm in inner diameter, and dried to prepare a cast film.

COMPARATIVE EXAMPLE 2

A cast film was prepared in the same manner as in Example 5 except that cystine was eliminated from Example 5.

TEST EXAMPLE 3

Figure 6A:
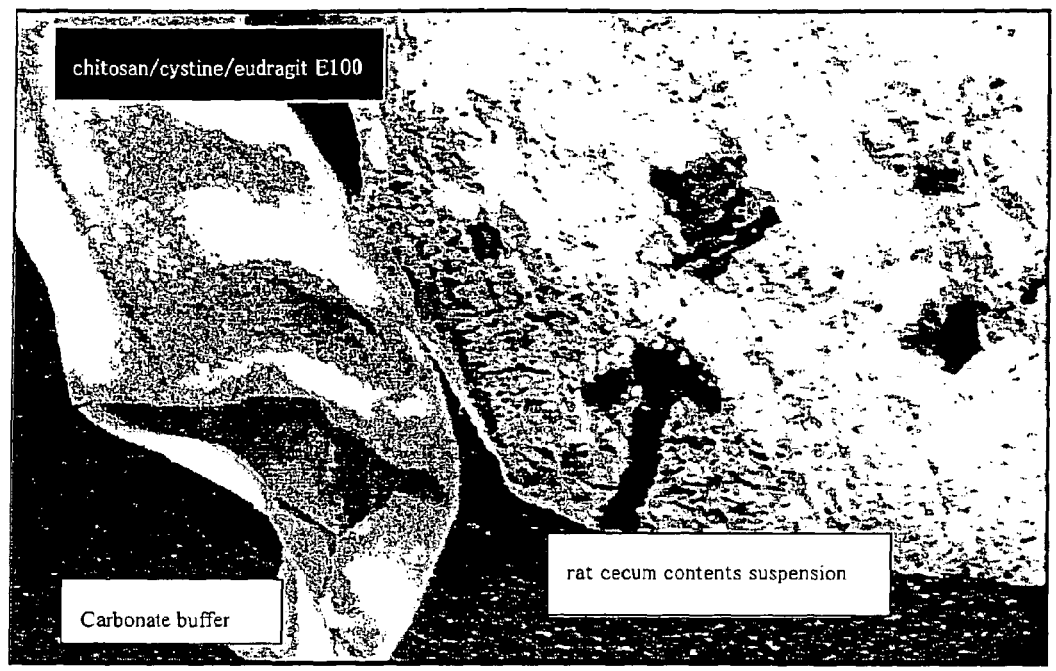
FIG. 6 is a photograph taken by use of a digital microscope, showing results of disintegration tests of the cast film prepared in Example 5 and the cast film of comparative composition. (a) represents the cast film prepared in Example 5 and (b) represents the cast film prepared in Comparative Example 2. In each photograph, left-hand side (film looking white) indicates results of shaking in carbonate buffer and right hand side indicates results of shaking in the suspension of cecum contents.
Figure 6B:
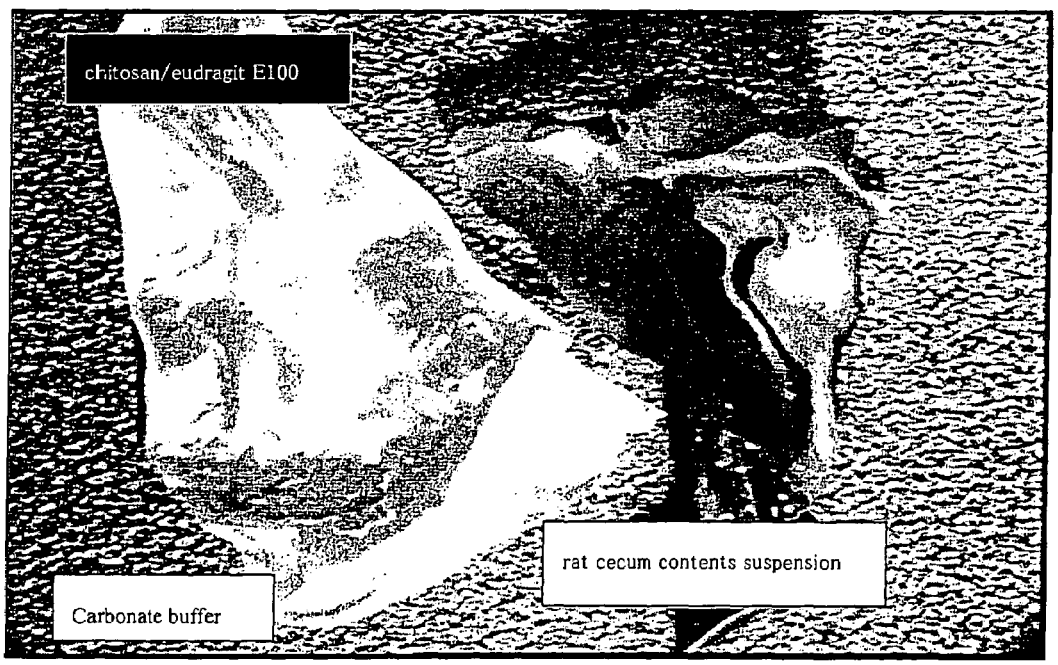

The cast films prepared in Example 5 and Comparative Example 2 above were subjected to shaking test in a suspension of cecum contents and carbonate buffer in the same manner as in Test Example 1. Digital microscopic images of the results obtained are shown in FIG. 6. FIG. 6(a) relates to the cast film prepared in Example 5 and FIG. 6(b) relates to the cast film prepared in Comparative Example 2. In each image, the left hand side (film looking white) shows the results of shaking in the carbonate buffer and the right hand side shows the results of shaking in the suspension of cecum contents.

The black fragment in mat paper background on the right hand side in FIG. 6(a) shows the cast film obtained from the composition of the present invention. It was demonstrated that the film was blackened and completely disintegrated by dipping it in the suspension of cecum contents.

EXAMPLE 6

The suspension prepared in Example 5 was used as a coating liquid.

In No. 3 gelatin hard capsules provided with a band seal were each filled 20 mg of theophylline as a model drug and 40 mg of magnesium stearate as an leakage inhibitor of theophylline in the small intestine. To this was sprayed the coating liquid prepared as above using a coating apparatus (Doria Coater 200, Powrex Corporation) to coat the capsules.

Then, the coated capsules were placed in a thermohygrostat set to 40° C. and 75% and subjected to humidification treatment for 24 hours.

TEST EXAMPLE 4

To confirm the resistance in small intestine, the coating capsules obtained in Example 6 were subjected to elution tests by the paddle test in accordance with Japan Pharmacopoeia Elution Test.

The test solution was Japan Pharmacopoeia second liquid (pH 6.8) and paddle rotation number was 50 rpm.

In the Japan Pharmacopoeia second liquid, which was a simulated intestinal juice, the capsules in Example 6 showed a very low leakage ratio of theophylline. As a result, it was demonstrated that the capsules of the present invention showed resistance in the small intestine. The results obtained are shown below.

TABLE 2

Small Intestine Resistance Test

| Time | Elution ratio of theophylline (%) | | |
|---|---|---|---|
| | No. 1 | No. 2 | Average |
| 0 hr | 0 | 0 | 0 |
| 1 hr | 0.3 | 0.2 | 0.3 |
| 2 hr | 1.7 | 2.0 | 1.9 |
| 3 hr | 4.8 | 5.3 | 5.1 |
| 4 hr | 7.8 | 8.2 | 8.0 |

TEST EXAMPLE 5

The capsules of Example 6 were placed in a No. 1 enteric capsule (Freund Sangyo) and further 10 mg of acetoaminophenone as a marker for indicating arrival at small intestine and 50 mg of sulfasalazine as a marker for indicating arrival at colon were added thereto. The connected portion of the capsule was sealed with a solution of hydroxypropylmethylcellulose acetate succinate, which was a raw material of capsule, in a mixed solution of methylene chloride/ethanol (1:1).

The capsule was orally administered to a dog together with 30 ml of water and the dog was collected the blood chronologically and the concentration of drug in the obtained plasma was measured. The dog was intravenously injected with atropin sulfate as an enteromotility suppressor 30 minutes before the oral administration in order to make uniform the rate of movement of capsule in the gastrointestinal tract. Sulfasalazine as the marker for indicating arrival at colon was decomposed by the enterobacteria after the arrival at the colon to release sulfapyridine as a decomposition product.

Figure 7:
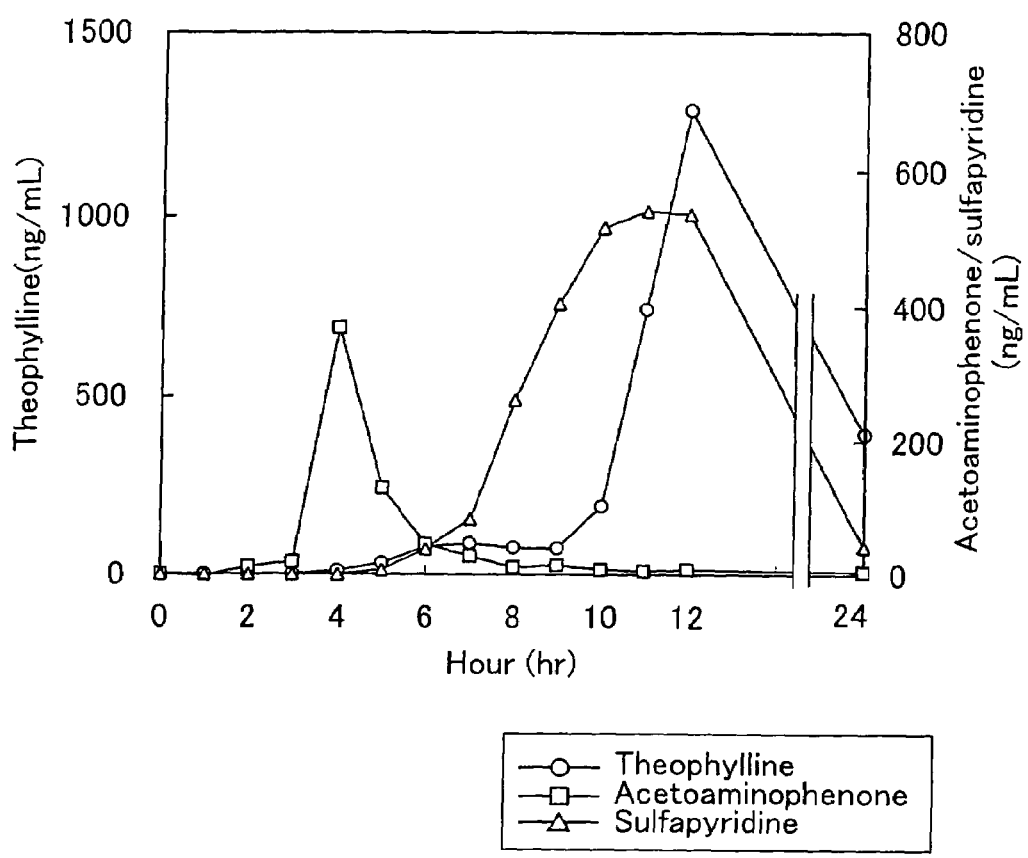
FIG. 7 is a diagram illustrating chronological blood levels of a model drug and a marker drug after administration of the coated capsules in Example 6 to a dog.

By measuring the blood level of sulfapyridine, an indication of arrival at colon of capsule was obtained. The blood level changes of the model drug and marker substances are shown in FIG. 7.

Since theophylline appeared later than the appearance of sulfapyridine in blood, it was confirmed that the capsule coated in Example 6 had resistance in small intestine and further that the capsule was disintegrated to release the contents after a while after its arrival at the colon.

As described above, it was demonstrated that the cast films formulated in soft capsules of the present invention were corroded on their surface by dipping them in a suspension of cecum contents. The dry weight of the cast film corroded in the suspension of cecum contents decreased as compared with the dry weight of the cast film of which no corrosion was observed in the carbonate buffer. Further, the seamless soft capsules containing cystine and chitosan in the capsule film according to the present invention did not disintegrate in the upper gastrointestinal tract to the ileum and no leakage of the content liquid was observed, so that they had high film strength. In the cecum and colon, the film strength of the capsule decreased and disintegration of the capsule and leakage of the content liquid occurred.

It was demonstrated that the cast films formulated in film coating according to the present invention were blackened and disintegrated completely by dipping them in the suspension of cecum contents.

The film coating capsules of the present invention showed suppressed leakage of the content liquid in elution tests using Japan Pharmacopoeia second liquid and further in the experiment of administration to a dog, they showed retarded release as compared with that of the marker indicating arrival at colon. This indicated that there occurred colon-specific release.

Therefore, by use of the composition for disintegration in lower gastrointestinal tract according to the present invention, the content can be delivered unfailingly, quickly and selectively in lower gastrointestinal tract utilizing enterobacteria that can be considered to have high specificity for targeting the lower gastrointestinal tract without being influenced by a change in pH due to a variation in bacterial flora.

INDUSTRIAL APPLICABILITY

By use of the composition for disintegration in lower gastrointestinal tract according to the present invention, that is, a composition for disintegration in lower gastrointestinal tract, comprising a compound <A> having a molecular weight of 1,000 or less and having a disulfide bond and a polymer <B> having a molecular weight of above 1,000 and having a property of being decomposed by enterobacteria, and/or a property of being softened, swelled or dissolved due to a decrease in pH, the content can be delivered unfailingly, quickly and selectively in lower gastrointestinal tract utilizing enterobacteria without being influenced by a change in pH due to a variation in bacterial flora. Therefore, the preparation using the composition for disintegration in lower gastrointestinal tract according to the present invention enables local accumulation of the drug in treating local gastrointestinal tract diseases such as ulcerative colitis and Crohn's disease, and therefore it is useful for improving the therapeutic effect.

Since no release of drug occurs before arrival at the lower gastrointestinal tract, side effects due to systemic circulation of the drug are decreased, and loss of the drug before it reaches the site where it is effective can be prevented. Therefore, the present invention is useful for improving the therapeutic effect.

Since use of the disintegrable composition of the present invention can prolong the residence time i.e., absorption effective time, in the colon, of a drug that has the property of exhibiting the efficacy after its transfer in systemic circulation, the colon can be utilized as an absorption site therefor. The colon secretes no gastrointestinal enzyme and the peptidase activity of mucous membrane of large intestine is low as compared with that of small intestine. Accordingly, especially a peptide- or protein-based drug, when it is released in the colon, is hardly metabolized by the enzymes, so that higher biological availability can be obtained.

The system for peroral uptake of a material desired to be delivered to lower gastrointestinal tract and selective release in the lower gastrointestinal tract according to the present invention can be used as a preferred example for the improvement of bioavailability for drugs that show decreased bioavailability due to high first pass effects when they are absorbed in the small intestine or due to inhibited absorption as a result of the interaction with undigested food or components of gastrointestinal juice in the small intestine. In addition, the drugs that are influenced by the drug-metabolizing enzyme in the upper gastrointestinal tract when absorbed in the small intestine are used as a preferred example in which a drug is released and absorbed in the rectum portion of the large intestine.

Furthermore, the system of the present invention can be used in diagnosis using a sustained release preparation, X-ray and NMR imaging technology or in health-care foods (functional foods).

What is claimed is:

1. A preparation for releasing a material selectively in a large intestine part of a lower gastrointestinal tract, comprising:
    (1) an inner core comprising a material to be delivered to the large intestine;
    (2) a disintegration layer surrounding said inner core, wherein said disintegration layer comprises a matrix comprising chitosan and particles of cystine dispersed in said matrix; and
    (3) an enteric coating surrounding said disintegration layer.

2. The preparation of claim 1, wherein the disintegration layer comprises cystine and chitosan in a ratio of 10/90 w/w to 90/10 W/W.

3. The preparation of claim 1, wherein the preparation is a pharmaceutical composition and the material is an active-ingredient for therapeutic use.

4. The preparation of claim 1, wherein the disintegration layer is in the form of a capsule or a coating layer.

5. The preparation of claim 1, wherein the inner core is in the form of a tablet or granule and the disintegration layer is in the form of a coating layer.

6. The preparation of claim 1, wherein the matrix containing chitosan further comprises a substance that controls disintegration rate of the disintegration layer in the large intestine of the lower gastrointestinal tract.

7. The preparation of claim 6, wherein the substance that controls the disintegration rate of the disintegration layer in the large intestine of the lower gastrointestinal tract is at least one substance selected from the group consisting of agar, pectin metal salt, carrageenin, gelatin, pectin, starch, cellulose, dimethylaminoethyl methacrylate/methylmethacrylate/butylmethacrylate copolymer and polyvinylacetal diethylaminoacetate.

8. A method for delivering a material selectively to a large intestine part of a lower gastrointestinal tract, comprising the steps of:
    (a) orally administering the preparation according to claim 1 to a patient;
    (b) dissolving the enteric polymer film in the small intestine;
    (c) forming microfine holes in the matrix where particles of cystine are present; and
    (d) disintegrating the matrix to selectively release the material in the large intestine.

* * * * *